(12) United States Patent
Horisaka et al.

(10) Patent No.: US 8,398,836 B2
(45) Date of Patent: Mar. 19, 2013

(54) GAS SENSOR

(75) Inventors: Sumiko Horisaka, Nagoya (JP); Sang Jae Lee, Ama-Gun (JP); Kosuke Nakagawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 203 days.

(21) Appl. No.: 12/853,527

(22) Filed: Aug. 10, 2010

(65) Prior Publication Data

US 2011/0036715 A1 Feb. 17, 2011

(30) Foreign Application Priority Data

Aug. 17, 2009 (JP) ................................. 2009-188271

(51) Int. Cl.
*G01N 27/41* (2006.01)
(52) U.S. Cl. ........................................ 204/424; 204/426
(58) Field of Classification Search .................. 204/425, 204/426; 205/781, 784.5
See application file for complete search history.

(56) References Cited

U.S. PATENT DOCUMENTS

| | | | |
|---|---|---|---|
| 4,722,778 A | 2/1988 | Hayakawa et al. | |
| 5,522,979 A * | 6/1996 | Tatumoto et al. | 204/429 |
| 5,993,625 A | 11/1999 | Inoue et al. | |
| 6,205,843 B1 * | 3/2001 | Tanaka et al. | 73/31.06 |
| 6,224,727 B1 * | 5/2001 | Miyata et al. | 204/425 |
| 6,340,419 B1 | 1/2002 | Nakae et al. | |
| 2003/0201172 A1 | 10/2003 | Nakagaki et al. | |
| 2004/0069629 A1 | 4/2004 | Tanaka et al. | |
| 2004/0217002 A1 | 11/2004 | Naito et al. | |
| 2009/0117007 A1 | 5/2009 | Furuta et al. | |

FOREIGN PATENT DOCUMENTS

| | | |
|---|---|---|
| EP | 0 678 740 A1 | 10/1995 |
| EP | 0 810 430 A2 | 12/1997 |
| JP | 62-190459 A1 | 8/1987 |
| JP | 02-062955 A1 | 3/1990 |
| JP | 08-271476 A1 | 10/1996 |
| JP | 09-311120 A1 | 12/1997 |
| JP | 11-108887 A1 | 4/1999 |
| JP | 2000-065782 A1 | 3/2000 |
| JP | 2003-090820 A1 | 3/2003 |
| JP | 2003-322636 A1 | 11/2003 |
| JP | 2004-333205 A1 | 11/2004 |
| JP | 2009-115618 A1 | 5/2009 |

OTHER PUBLICATIONS

Japanese Final Office Action dated Jan. 24, 2012 (with partial English translation).

* cited by examiner

*Primary Examiner* — Alex Noguerola
(74) *Attorney, Agent, or Firm* — Burr & Brown

(57) ABSTRACT

A gas sensor having a sensor element that includes an inner space for introducing a measurement gas therein from an external space and a pump cell which has a first electrode formed on a surface of the inner space and a second electrode formed in a space different from the inner space and is provided to pump oxygen out of the inner space by applying a predetermined voltage between the first electrode and the second electrode. Assuming that the length of the inner space in a short-side direction of the sensor element as viewed from the front end portion side thereof is x1 and the length of the inner space in a longitudinal direction of the sensor element as viewed from the front end portion side thereof is x2, the following inequality is satisfied: $0.05 \leq x1/x2 \leq 0.25$.

19 Claims, 5 Drawing Sheets

F I G. 7
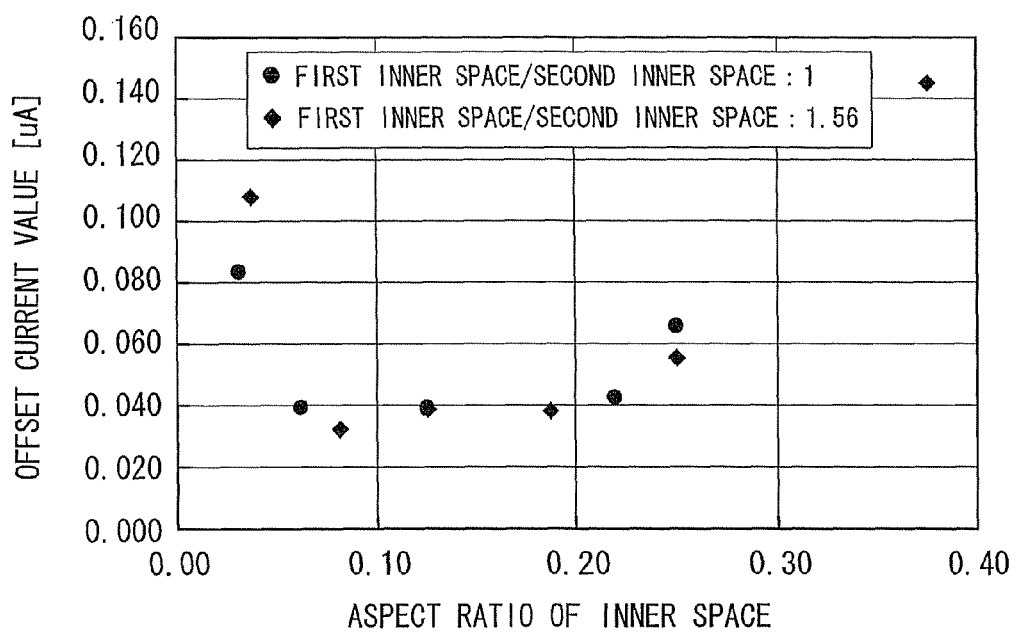

US 8,398,836 B2

GAS SENSOR

BACKGROUND OF THE INVENTION

1. Field of the Invention

The present invention relates to a gas sensor which comprises a sensor element and measures a predetermined gas component in a measurement gas, and more particularly to an arrangement of an inner space of the sensor element.

2. Description of the Background Art

Conventionally, in order to know the concentration of a desired gas component in a measurement gas, various measuring devices have been used. As a device for measuring the nitrogen oxide (NOx) concentration in a measurement gas such as burned gas or the like, for example, a gas sensor is well known, which has an electrochemical pump cell having a structure in which a platinum (Pt) electrode and a rhodium (Rh) electrode are Banned on a solid electrolyte layer having oxygen ion conductivity, such as zirconia ($ZrO_2$) or the like (see, for example, Japanese Patent Application Laid Open Gazette No. 8-271476). In such a gas sensor, an inner space for measuring a predetermined gas component in a measurement gas is formed in a sensor element.

In the gas sensor, the measurement of the NOx concentration in the measurement gas is conducted, for example, as follows: a pump cell provided in a first inner space communicating with an external space controls the oxygen concentration, a nitrogen oxide (NOx) is reduced or decomposed in a second inner space communicating with the first inner space, and a pump current flowing in a measuring pump cell provided in the second inner space is measured.

In the above gas sensor, however, the temperature distribution inside the sensor element is sometimes varied because of decrease in the surface temperature of the sensor element due to the effect of the decrease in the temperature, the variation in the flow velocity or the like of the measurement gas. When the temperature distribution inside the sensor element varies, the impedance or the like of the pump cell provided in the inner space varies, and consequently the measured current flowing in the measuring pump cell fluctuates though the NOx concentration is not essentially changed. In summary, the above-discussed gas sensor has the problem that the variation in the temperature distribution inside the sensor element causes fluctuation of measured values in the gas sensor.

Further, in the above-discussed gas sensor, the pumping capability of the pump cell for controlling the oxygen concentration inside the inner space depends on the effect of the distribution of the oxygen concentration or the temperature distribution inside the inner space. The decrease in the pumping capability of the pump cell raises the fluctuation of an offset current included in the measured current due to oxygen remaining near a measuring electrode, even when no nitrogen oxide (NOx) exists. Then, the fluctuation of the offset current results in an instability of the measured current flowing during the measurement of the NOx concentration. In summary, the above-discussed gas sensor has the problem that the effect of the distribution of the oxygen concentration or the temperature distribution inside the inner space causes variation of measured values.

SUMMARY OF THE INVENTION

The present invention is intended for a sensor element of a gas sensor for measuring a predetermined gas component in a measurement gas, and more particularly relates to an arrangement of an inner space of the sensor element.

According to the present invention, the sensor element of a gas sensor for detecting a predetermined gas component in a measurement gas comprises a solid electrolyte body formed mainly of an oxygen ion conductive solid electrolyte, an inner space for introducing a measurement gas therein from an external space, and a pump cell having a first electrode and a second electrode, for pumping oxygen out of the inner space by applying a predetermined voltage between the first electrode and the second electrode, the first electrode being formed on a surface of the inner space and the second electrode being formed in a space different from the inner space, and in the sensor element, assuming that the length of the inner space in a short-side direction of the sensor element as viewed from the front end portion side thereof is x1 and the length of the inner space in a longitudinal direction thereof is x2, $0.05 \leq x1/x2 \leq 0.25$.

Herewith, since the effect of the distribution of the oxygen concentration and the effect of the temperature distribution inside the inner space to measured values are reduced in the gas sensor, it is possible to realize the gas sensor in which the variation of the measured values is reduced.

Preferably, in the present invention, the distance from a surface of the sensor element in the short-side direction thereof to said inner space is 10% or more of the length of said sensor element in said short-side direction thereof.

It is thereby possible to realize the gas sensor in which the variation of the measured values is reduced even if the surface of the sensor element is cooled due to the effect of the temperature, the flow velocity and the like of the measurement gas.

Therefore, it is an object of the present invention to provide a gas sensor in which the variation of the measured values is reduced.

These and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a graph showing relations between the aspect ratio of the inner space (the thickness of the inner space/the width of the inner space) and the offset current.

DESCRIPTION OF THE PREFERRED EMBODIMENTS

<Schematic Configuration of Gas Sensor>

First, a description will be made of a schematic configuration of a gas sensor 100.

Figure 1:
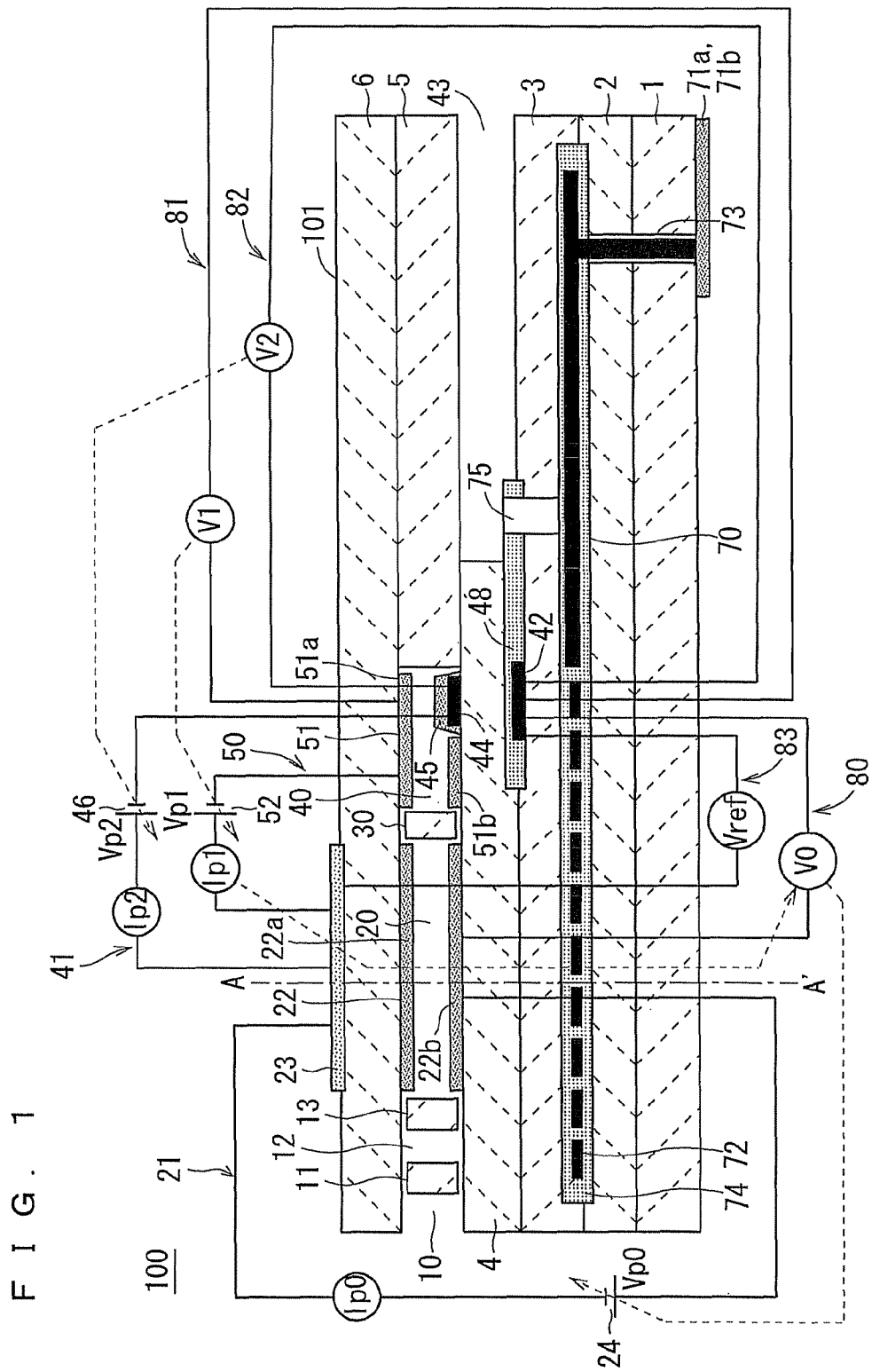
FIG. 1 is a partially sectional view schematically showing an exemplary configuration of a gas sensor in accordance with a preferred embodiment of the present invention.

FIG. 1 is a schematic cross-sectional view schematically showing one example of the configuration of the gas sensor 100. A sensor 101 is an elongated element of a plate-shaped configuration having a structure in which six layers of a first substrate layer 1, a second substrate layer 2, a third substrate layer 3, a first solid electrolyte layer 4, a spacer layer 5, and a second solid electrolyte layer 6 are laminated in this order from the lower side in the drawing, each of the layers being composed of an oxygen ion conducting solid electrolyte layers such as zirconia ($ZrO_2$). In addition, the solid electrolyte configuring those six layers is densely airtight. The sensor element 101 is provided in such a manner that after a predetermined process and printing of a circuit pattern are performed on a ceramic green sheet corresponding to each layer, they are laminated and integrated by baking.

A gas inlet 10, a first diffusion-controlling part 11, a buffer space 12, a second diffusion-controlling part 13, a first inner space 20, a third diffusion-controlling part 30, and a second inner space 40 are adjacently formed so as to be communicated in this order between a lower surface of the second solid electrolyte layer 6 and an upper surface of the first solid electrolyte layer 4, at one end of the sensor element 101.

The gas inlet 10, the buffer space 12, the first inner space 20, and the second inner space 40 are internal spaces provided by hollowing the spacer layer 5 in the sensor element 101, in which their upper parts are defined by the lower surface of the second solid electrolyte layer 6, their lower parts are defined by the upper surface of the first solid electrolyte layer 4, and their side parts are defined by a side surface of the spacer layer 5.

Each of the first diffusion-controlling part 11, the second diffusion-controlling part 13, and the third diffusion-controlling part 30 is provided as two horizontally long (an opening has a longitudinal direction in a direction perpendicular to the drawing) slits. In addition, a portion from the gas inlet 10 to the second inner space 40 is also referred to as a gas distribution part.

In addition, in a position more distant from the end side than the gas distribution part, a reference gas inlet space 43 is provided between an upper surface of the third substrate layer 3 and a lower surface of the spacer layer 5, in which its side part is defined by a side surface of the first solid electrolyte layer 4. For example, the air is introduced to the reference gas inlet space 43 as a reference gas in measuring the NOx concentration.

An air inlet layer 48 is composed of porous alumina, and the reference gas is introduced to the air inlet layer 48 through the reference gas inlet space 43. In addition, the air inlet layer 48 is formed to cover a reference electrode 42.

The reference electrode 42 is formed so as to be sandwiched between the upper surface of the third substrate layer 3 and the first solid electrolyte layer 4, and as described above, the air inlet layer 48 leading to the reference gas inlet space 43 is provided around the reference electrode 42. In addition, as will be described below, an oxygen concentration (oxygen partial pressure) in the first inner space 20 or the second inner space 40 can be measured using the reference electrode 42.

The gas inlet 10 is a portion open to an external space in the gas distribution part, and a measurement gas is introduced from the external space into the sensor element 101 through the gas inlet 10.

The first diffusion-controlling part 11 is a portion to apply a predetermined diffusion resistance to the measurement gas which is brought in from the gas inlet 10.

The buffer space 12 is a space provided to guide the introduced measurement gas from the first diffusion-controlling part 11 to the second diffusion-controlling part 13.

The second diffusion-controlling part 13 is a portion to apply a predetermined diffusion resistance to the measurement gas which is introduced from the buffer space 12 to the first inner space 20.

When the measurement gas is introduced from the outside the sensor element 101 to the first inner space 20, the measurement gas which was abruptly introduced from the gas inlet 10 into the sensor element 101 due to pressure fluctuation of the measurement gas in the outer space (pulsation of exhaust pressure in the case that the measurement gas is an exhaust gas of a car) is not directly introduced into the first inner space 20 but introduced into the first inner space 20 after the concentration fluctuation of the measurement gas has been negated through the first diffusion-controlling part 11, the buffer space 12, and the second diffusion-controlling part 13. Accordingly, the concentration fluctuation of the measurement gas is negligibly small when the gas is introduced to the first internal space.

The first inner space 20 is provided as a space to adjust an oxygen partial pressure in the measurement gas which has been introduced through the second diffusion-controlling part 13. The oxygen partial pressure is adjusted by an operation of a main pump cell 21.

The main pump cell 21 is an electrochemical pump cell including an inner pump electrode 22 having a ceiling electrode part 22a provided on almost all over the lower surface of the second solid electrolyte layer 6 which faces the first inner space 20, an outer pump electrode 23 provided on the upper surface of the second solid electrolyte layer 6 so as to be exposed to the external space and opposed to the ceiling electrode part 22a, and the second solid electrolyte layer 6 sandwiched between the above electrodes.

The inner pump electrode 22 lie astride the upper and lower solid electrolyte layers (second solid electrolyte layer 6 and the first solid electrolyte layer 4) to define the first inner space 20, and the spacer layer 5 to define the side wall thereof. More specifically, the ceiling electrode part 22a is formed on the lower surface of the second solid electrolyte layer 6 to define a ceiling surface of the first inner space 20, a bottom electrode part 22b is formed on the upper surface of the first solid electrolyte layer 4 to define a bottom surface thereof, and a side electrode part (not shown) is formed on a side wall surface (inner surface) of the spacer layer 5 to define each side wall of the first inner space 20, so as to connect the ceiling electrode part 22a to the bottom electrode part 22b, so that a structure having a tunnel configuration at the portion of the side electrode part is provided.

Each of the inner pump electrode 22 and the outer pump electrode 23 is formed as a porous cermet electrode (cermet electrode including Pt containing Au by 1% and zirconia). However, the inner pump electrode 22 which is in contact with the measurement gas is formed of a material whose reducing ability with respect to NOx component in the measurement gas is weakened. The inner pump electrode 22 will be described in detail below.

The main pump cell 21 can pump out the oxygen in the first inner space 20 to the external space, or pump in the oxygen in the external space into the first inner space 20 by means of applying a desired pump voltage Vp0 between the inner pump electrode 22 and the outer pump electrode 23 so as to generate a pump current Ip0 in a positive direction or negative direction between the inner pump electrode 22 and the outer pump electrode 23.

Moreover, in order to detect the oxygen concentration (oxygen partial pressure) in the atmosphere of the first inner space 20, an electrochemical sensor cell, that is, a main-pump-controlling oxygen-partial-pressure detection sensor cell 80 includes the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first inner space 20 can be found by measuring an electromotive force V0 in the main-pump-controlling oxygen-partial-pressure detection sensor cell 80. Furthermore, the pump current Ip0 is controlled by feedback-controlling the Vp0 to keep the electromotive force constant. Thus, the oxygen concentration in the first inner space 20 can be kept at a predetermined value.

The first diffusion-controlling part 30 is a portion to apply a predetermined diffusion resistance to the measurement gas whose oxygen concentration (oxygen partial pressure) has been controlled in the first inner space 20 by the operation of the main pump cell 21, and introduces the measurement gas to the second inner space 40.

The second inner space 40 is provided to perform an operation regarding the measurement of a nitrogen oxide (NOx) concentration in the measurement gas which has been introduced through the third diffusion-controlling part 30. The NOx concentration is mainly measured in the second inner space 40 whose oxygen concentration has been adjusted by an auxiliary pump cell 50, by an operation of a measurement pump cell 41.

After the oxygen concentration (oxygen partial pressure) has been previously adjusted in the first inner space 20, the oxygen partial pressure of the measurement gas which has been introduced through the third diffusion-controlling part is further adjusted by the auxiliary pump cell 50 in the second inner space 40. Therefore, since the oxygen concentration in the second inner space 40 can be kept constant with a high degree of accuracy, the gas sensor 100 can measure the NOx concentration with a high degree of accuracy.

The auxiliary pump cell 50 is an auxiliary electrochemical pump cell including an auxiliary pump electrode 51 having a ceiling electrode part 51a provided on almost a whole lower surface of the second solid electrolyte layer 6 which faces the second inner space 40, the outer pump electrode 23 (not limited to the outer pump electrode 23 but may be an appropriate electrode positioned outside the sensor element 101), and the second solid electrolyte layer 6.

The auxiliary pump electrode 51 is provided in the second inner space 40 so as to have a tunnel structure similar to the inner pump electrode 22 provided in the first inner space 20. That is, the ceiling electrode part 51a is formed on the second solid electrolyte layer 6 defining a ceiling surface of the second inner space 40, a bottom electrode part 51b is formed on the first solid electrolyte layer 4 defining a bottom surface of the second inner space 40, and a side electrode part (not shown) to connect the ceiling electrode part 51a to the bottom electrode part 51b is provided on each wall surface of the spacer layer 5 defining a side wall of the second inner space 40.

In addition, the auxiliary pump electrode 51 is also formed of a material whose reducing ability with respect to the NOx component in the measurement gas is weakened, similar to the inner pump electrode 22.

The auxiliary pump cell 50 can pump out the oxygen in the atmosphere of the second inner space 40 to the external space, or pump in the oxygen in the external space into the second inner space 40 by means of applying a desired pump voltage Vp1 between the auxiliary pump electrode 51 and the outer pump electrode 23.

Moreover, in order to control the oxygen partial pressure in the atmosphere of the second inner space 40, an auxiliary-pump-controlling oxygen-partial-pressure detection sensor cell 81 includes the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 is pumped by a variable power supply 52 whose voltage is controlled based on an electromotive force V1 detected by the auxiliary-pump-controlling oxygen-partial-pressure detection sensor cell 81. Thus, the oxygen partial pressure in the atmosphere of the second inner space 40 can be lowered so as not to substantially affect the measurement of NOx.

In addition, at the same time, its pump current Ip1 is used to control the electromotive force of the main-pump-controlling oxygen-partial-pressure detection sensor cell 80. More specifically, the pump current Ip1 is inputted to the main-pump-controlling oxygen-partial-pressure detection sensor cell 80 as a control signal and then its electromotive force V0 is controlled, so that an inclination of the oxygen partial pressure in the measurement gas which is introduced from the third diffusion-controlling part 30 to the second inner space 40 is controlled to be always kept constant. When used as the NOx sensor, the oxygen concentration in the second inner space 40 is kept at a constant value such as about 0.001 ppm, by the operations of the main pump cell 21 and the auxiliary pump cell 50.

The measuring pump cell 41 measures the NOx concentration in the measurement gas, in the second inner space 40. The measuring pump cell 41 is an electrochemical pump cell including a measurement electrode 44 provided on the upper surface of the first solid electrolyte layer 4 which faces the second inner space 40 so as to be apart from the third diffusion-controlling part 30, the outer pump electrode 23, the second solid electrolyte layer 6, the spacer layer 5, and the first solid electrolyte layer 4.

The measurement electrode 44 is a porous cermet electrode which has an almost-rectangular shape in a plan view. The measurement electrode 44 also functions as a NOx reducing catalyst to reduce NOx existing in the atmosphere of the second inner space 40. Furthermore, the measurement electrode 44 is covered with a fourth diffusion-controlling part 45.

The fourth diffusion-controlling part 45 is a film made of a porous body mostly including alumina ($Al_2O_3$). The fourth diffusion-controlling part 45 takes a roll in limiting a NOx amount flowing into the measurement electrode 44, and also functions as a protection film of the measurement electrode 44.

The measuring pump cell 41 pumps out the oxygen generated due to decomposition of the nitrogen oxide in the atmosphere around the measurement electrode 44, and can detect its generation amount as a pump current Ip2.

Moreover, in order to detect an oxygen partial pressure around the measurement electrode 44, an electrochemical sensor cell, that is, a measuring-pump-controlling oxygen-partial-pressure detection sensor cell 82 includes the second solid electrolyte layer 6, the spacer layer 5, the first solid electrolyte layer 4, the third substrate layer 3, the measurement electrode 44, and the reference electrode 42. A variable power supply 46 is controlled based on a control voltage V2 detected by the measuring-pump-controlling oxygen-partial-pressure detection sensor cell 82.

The measurement gas which has been introduced in the second inner space 40 reaches the measurement electrode 44 through the fourth diffusion-controlling part 45 under the condition that its oxygen partial pressure is controlled. The nitrogen oxide in the measurement gas around the measurement electrode 44 is reduced and oxygen is generated ($2NO \rightarrow N_2+O_2$). Thus, the generated oxygen is pumped by the measuring pump cell 41, and at this time a voltage Vp2 of the variable power supply is controlled so that the control voltage V2 detected by the measuring-pump-controlling oxygen-partial-pressure detection sensor cell 82 can be kept constant. Since the amount of oxygen generated around the measurement electrode 44 is proportional to the concentration of the nitrogen oxide in the measurement gas, the concentration of the nitrogen oxide in the measurement gas is calculated using the pump current Ip2 in the measuring pump cell 41.

In addition, if oxygen partial pressure detecting means is provided by combining the measurement electrode 42, the first solid electrolyte layer 4, the third substrate layer 3, and the reference electrode 44, as an electrochemical sensor cell, an electromotive force can be detected based on a difference between the oxygen amount generated due to the reduction of the NOx component in the atmosphere around the measurement electrode 44 and an oxygen amount in the reference air, and as a result, the concentration of the NOx component in the measurement gas can be found.

What is more, an electrochemical sensor cell 83 is constituted of the second solid electrolyte layer 6, the spacer layer 5, the first solid electrolyte layer 4, the third substrate layer 3, the outer pump electrode 23, and the reference electrode 42, and the oxygen partial pressure in the measurement gas outside the sensor can be detected by an electromotive force Vref obtained by this sensor cell 83.

In the gas sensor 100 having the above configuration, the measurement gas whose oxygen partial pressure is always kept at a constant low value (which does not affect the measurement of NOx substantially) by the operations of the main pump cell 21 and the auxiliary pump cell 50 is applied to the measuring pump cell 41. Therefore, the NOx concentration in the measurement gas can be known, based on the pump current Ip2 which flows on the basis that the oxygen generated by the reduction of NOx is pumped out by the measuring pump cell 41, in approximately proportion to the NOx concentration in the measurement gas.

Furthermore, in order to enhance oxygen ion conductivity of the solid electrolyte, the sensor element 101 has a heater part 70 taking a role of temperature regulation to heat the sensor element 101 and keep its temperature. The heater part 70 includes heater electrodes 71a and 71b, a heater 72, a through hole 73, a heater insulation layer 74, and a pressure diffusion hole 75.

The heater electrodes 71a and 71b are an electrode formed to be in contact with the lower surface of the first substrate layer 1. When the heater electrodes 71a and 71b are connected to an external power supply, a power can be supplied to the heater part 70 from the outside.

The heater 72 is an electric resistor formed to be sandwiched between the second substrate layer 2 and the third substrate layer 3 vertically. The heater 72 is connected to the heater electrode 71 through the through hole 73, and generates heat when a power is supplied from the outside through the heater electrode 71, and heats the solid electrolyte forming the sensor element 101 and keeps its temperature.

Then, the heater 72 is buried all over the region from the first inner space 20 to the second inner space 40, and can regulate the temperature in the whole sensor element 101 so that the solid electrolyte can be activated.

The heater insulation layer 74 is formed of an insulator such as alumina, on upper and lower surfaces of the heater 72. The heater insulation layer 74 is formed with a view to obtaining electric insulation between the second substrate layer 2 and the heater 72, and electric insulation between the third substrate layer 3 and the heater 72.

The pressure diffusion hole 75 is a portion configured to penetrate the third substrate layer 3 and communicate with the reference gas inlet space 43, and foamed with a view to lessening an inner pressure from rising with the temperature rise in the heater insulation layer 74.

<Formation Position and Shape of Inner Space>

Next, discussion will be made on formation positions and shapes of the first inner space 20 and the second inner space 40 in the sensor element 101.

Figure 2:
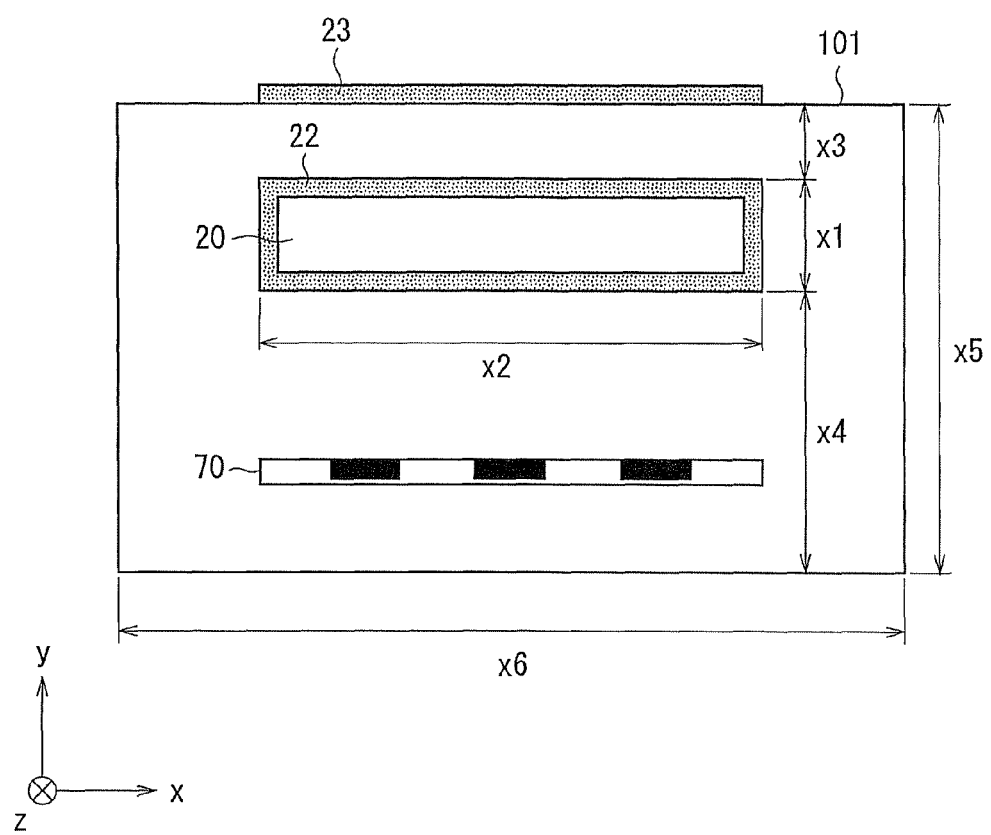
FIG. 2 is a view schematically showing the A-A' section of the gas sensor of FIG. 1 as viewed from the side of a reference gas introduction space.

FIG. 2 is a view schematically showing the A-A' section of the gas sensor 100 of FIG. 1 as viewed from the side of the reference gas inlet space 43. In the preferred embodiment, as discussed later, the formation position and the shape of the first inner space 20 will be discussed as an example, but if the gas sensor 100 has a plurality of inner spaces provided with pump cells, the same relation holds as to each of the inner spaces. In FIG. 2, for convenience of illustration, given is an xyz rectangular coordinate system with the horizontal (left and right) direction in this figure defined as an x-axis direction, the vertical (up and down) direction in this figure defined as a y-axis direction, and the direction perpendicular to this paper defined as a z-axis direction.

In FIG. 2, the length of the first inner space 20 in the cross-sectional short-side direction (y-axis direction) (hereinafter, described also as "the thickness of the first inner space 20") is represented by "x1" and the length of the first inner space 20 in the cross-sectional longitudinal direction (x-axis direction) (hereinafter, described also as "the width of the first inner space 20") is represented by "x2". The respective distances from the upper and lower surfaces of the sensor element 101 to the first inner space 20 are represented by "x3" and "x4". The length of the sensor element 101 in the cross-sectional short-side direction (y-axis direction) (hereinafter, described also as "the thickness of the sensor element 101") is represented by "x5" and the length of the sensor element 101 in the cross-sectional longitudinal direction (x-axis direction) (hereinafter, described also as "the width of the sensor element 101") is represented by "x6". Discussion will be made below on preferable ranges as to "x1" to "x4" defining the position and the size of the first inner space 20.

(Formation Position of Inner Space in Sensor Element)

First, discussion will be made on the formation position of the first inner space 20 in the sensor element 101.

As discussed above, in order to reduce the variation of measured values, it is necessary to suppress the change in the NOx sensitivity due to the variation of the pumping capability even if the surface temperature of the sensor element decreases due to the effect of the decrease in the temperature, the variation in the flow velocity or the like of the measurement gas.

The effect of the decrease in the surface temperature of the sensor element produced on the pump cell depends on the position of the inner space in the sensor element. This is because when the surface temperature of the sensor element decreases, the extent of the variation in the pumping capability due to the variation in the impedance or the like of the pump cell depends on the position of the inner space in the sensor element.

This means that it is possible to reduce the variation of measured values in the gas sensor by forming the inner space at such a position in the sensor element as to suppress the change in the NOx sensitivity due to the variation of the pumping capability even if the surface temperature of the sensor element decreases due to the effect of the decrease in the temperature, the variation in the flow velocity or the like of the measurement gas.

Figure 3:
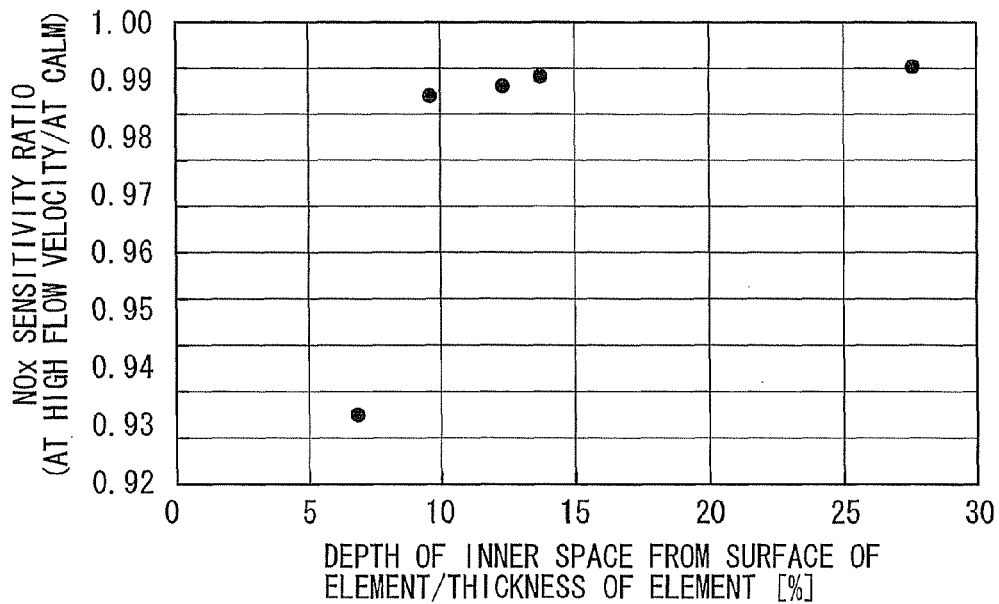
FIG. 3 is a graph showing a relation between the ratio of the length from a surface of a sensor element to an inner space with respect to the thickness of the element and the NOx sensitivity ratio.

FIG. 3 is a graph showing a relation between the ratio (x3/x5) of the length from the surface of the sensor element 101 to the first inner space 20 with respect to the thickness of the element and the NOx sensitivity ratio. In the preferred embodiment, the NOx sensitivity ratio refers to an index indicating the degree of variation in the NOx sensitivity caused by the difference in the flow velocity of the measurement gas and a value represented by the ratio of the NOx sensitivity at high flow velocity with respect to the NOx sensitivity at calm. It is herein assumed that a case where the flow velocity of the measurement gas is 15 m/s is defined as high flow velocity and a case where the flow velocity is 0.1 m/s or less is defined as calm.

As shown in FIG. 3, if x3/x5 is 10% or more, the NOx sensitivity ratio takes a value approximate to 1.00, being almost constant. In contrast to this, if x3/x5 is less than 10%, the NOx sensitivity ratio sharply decreases.

Thus, there is almost no dependence of the NOx sensitivity on the gas flow velocity when the first inner space 20 is located in a range where the distance from the surface of the sensor element 101 thereto is 10% or more of the thickness of the element. This means that when the first inner space 20 is located in this range, almost no effect of the decrease in the surface temperature of the sensor element 101 accompanying the change in the flow velocity of the measurement gas is produced on the pump cell.

On the other hand, when the first inner space 20 is located in the range where the distance from the surface of the sensor element 101 thereto is less than 10% of the thickness of the element, the dependence of the NOx sensitivity on the gas flow velocity increases. This means that when the first inner space 20 is located at a position where the variation in the temperature of the sensor element 101 is likely to be caused by the change in the flow velocity of the measurement gas, the pump performance is affected by the variation in the temperature and the measurement accuracy thereby decreases.

In view of the above fact, in the gas sensor 100 of the preferred embodiment, the first inner space 20 is located at the position where the ratio (x3/x5) of the length from the surface of the sensor element 101 to the first inner space 20 with respect to the thickness of the sensor element 101 is 10% or more. Thus, the gas sensor of the preferred embodiment is configured to reduce the variation of measured values even in a state where the surface temperature of the sensor element 101 decreases due to the effect of the decrease in the temperature, the variation in the flow velocity or the like of the measurement gas.

Though discussion has been made on the ratio (x3/x5) of the length from the front surface of the sensor element 101 to the first inner space 20 with respect to the thickness of the element in the preferred embodiment, the same applies to the ratio (x4/x5) of the length from the back surface of the sensor element 101 to the first inner space 20 with respect to the thickness of the element.

(Thickness of Inner Space)

Next, discussion will be made on the thickness (x1) of the first inner space 20.

In the gas sensor 100, the NOx concentration is calculated by using the fact that the pump current Ip2 is substantially proportional to the concentration of NOx present in the measurement gas, while keeping the oxygen partial pressure constant in the first inner space 20 and the second inner space 40. In terms of the pump current Ip2, a trace amount of current (offset current) flows even if the NOx concentration is 0 (even if there is no NOx present in the measurement gas). The offset current is generated by decomposition of oxygen remaining in very small amounts near the measuring electrode in the measurement gas.

As discussed above, in order to suppress the variation of measured values, it is necessary to reduce the effect of the decrease in the surface temperature of the sensor element 101 and lessen the amount of oxygen remaining near the measuring electrode, to thereby reduce the fluctuation in the offset current and minimize the offset current value.

The distribution of the oxygen concentration and that of the temperature in the inner space depend on the shape of the inner space. In other words, in the gas sensor, the pumping capability varies and the offset current fluctuates depending on the shape of the inner space.

This means that it is possible to reduce the variation of measured values in the gas sensor by forming the inner space to have such a shape as to lessen the offset current value.

Figure 4:
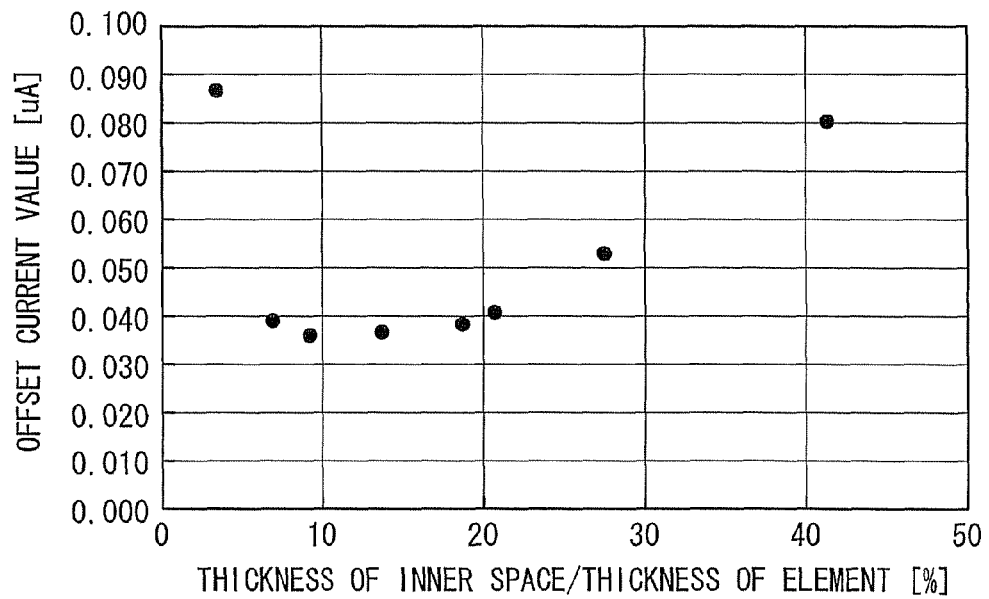
FIG. 4 is a graph showing a relation between the ratio of the thickness of the inner space with respect to the thickness of the sensor element and the offset current.

FIG. 4 is a graph showing a relation between the ratio of the thickness (x1) of the first inner space 20 with respect to the thickness (x5) of the sensor element and the offset current. As shown in FIG. 4, when the ratio (x1/x5) of the thickness of the first inner space 20 with respect to the thickness of the sensor element is in the range from 7% to 20%, the offset current takes an almost constant value of 0.04 pA or less. Particularly, when the ratio (x1/x5) of the thickness of the first inner space 20 with respect to the thickness of the sensor element is in the range from 10% to 18%, the offset current value is smaller. In contrast to this, when the ratio (x1/x5) of the thickness of the first inner space 20 with respect to the thickness of the sensor element is less than 7% or more than 20%, the offset current value sharply increases.

Thus, when the ratio (x1/x5) of the thickness of the first inner space 20 with respect to the thickness of the gas sensor is in the range from 7% to 20%, the offset current takes an almost constant value of 0.04 μA or less. This means that if the sensor element 101 is formed to have the above thickness, there is almost no variation in the pumping capability due to the distribution of the oxygen concentration and that of the temperature in the inner space.

On the other hand, when the ratio of the thickness of the first inner space 20 with respect to the thickness of the sensor element is more than 20%, the offset current value sharply increases. It is thought that this is because the nonuniformity in the temperature distribution of the first inner space 20 increases and the controllability of the pump cell on the oxygen concentration in the first inner space 20 is low. Further, also when the ratio of the thickness of the first inner space 20 with respect to the thickness of the sensor element is less than 7%, the offset current value sharply increases. It is thought that this is because the distribution of the oxygen concentration becomes remarkable in the first inner space 20 since the diffusion resistance of the gas in the first inner space 20 is large, and the controllability of the first pump cell on the oxygen concentration in the first inner space 20 thereby decreases.

In view of the above fact, in the gas sensor 100 of the preferred embodiment, it is favorable that the ratio (x1/x5) of the thickness of the first inner space 20 with respect to the thickness of the sensor element 101 should be in the range from 7% to 20%, and more preferably should be in the range from 10% to 18%. In the gas sensor 100 of the preferred embodiment, the offset current value thereby becomes smaller and the variation of measured values can be reduced.

Therefore, in the gas sensor 100 of the preferred embodiment, it is favorable that the first inner space 20 should have a thickness ranging from 7% to 20%, and more preferably ranging from 10% to 18%, with respect to the thickness of the sensor element 101 and should be arranged at a position where the length from the surface of the sensor element 101 thereto is 10% of the thickness of the sensor element 101.

Figure 5:
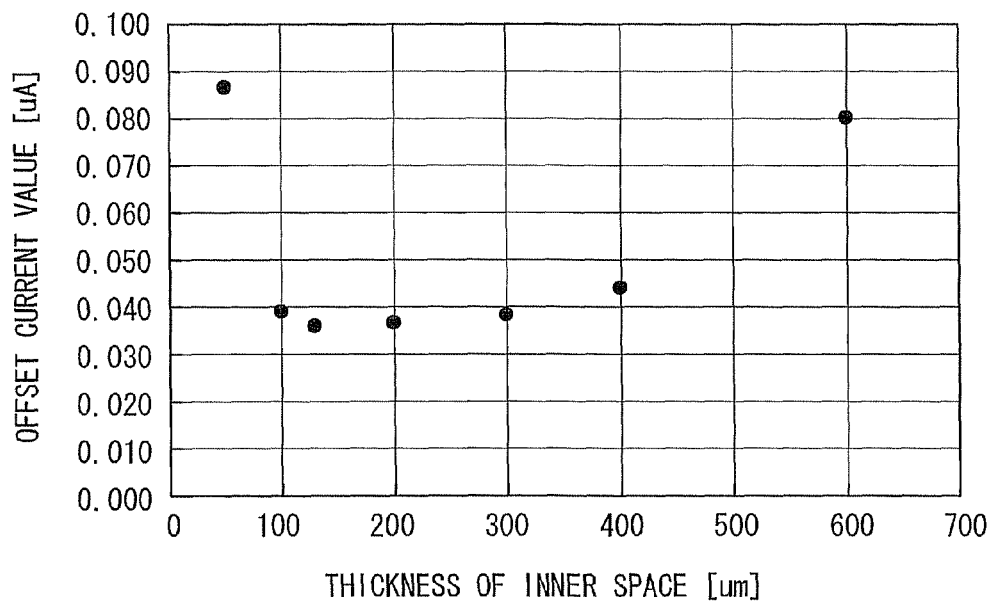
FIG. 5 is a graph showing a relation between the thickness of the inner space and the offset current.

FIG. 5 is a graph showing a relation between the thickness (x1) of the first inner space 20 and the offset current when the thickness (x5) of the sensor element is 1400 µm. As shown in FIG. 5, when the thickness (x5) of the sensor element is 1400 µm, if the thickness (x1) of the first inner space 20 is in the range from 100 µm to 400 µm, the offset current takes an almost constant small value. Particularly, if the thickness (x1) of the first inner space 20 is in the range from 130 µm to 250 µm, the offset current value becomes smaller.

(Relation Between Volume of Inner Space and Area of Pump Electrode)

Next, discussion will be made on a relation between the volume of the first inner space 20 and the area of the inner pump electrode 22.

Figure 6:
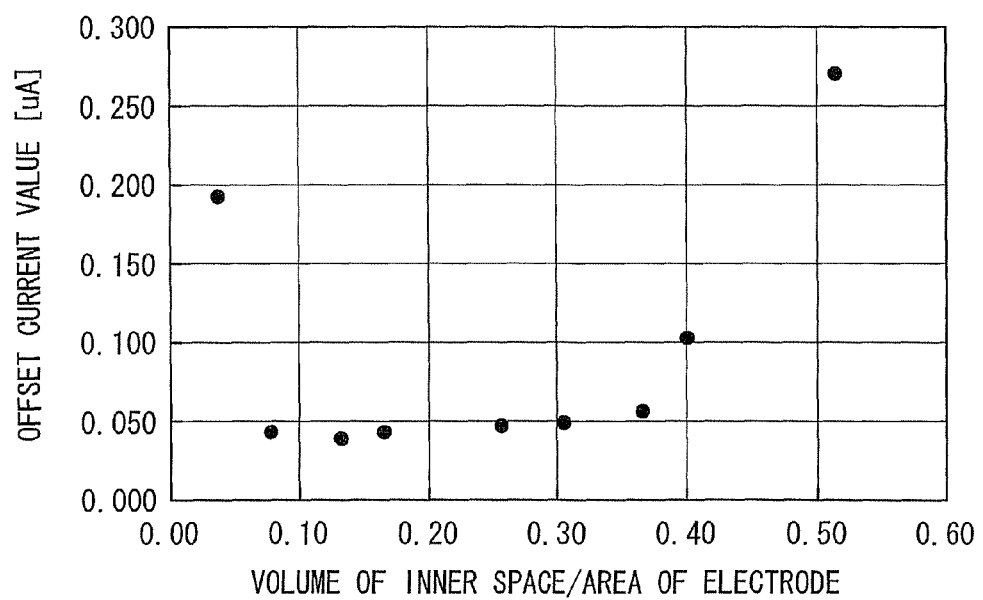
FIG. 6 is a graph showing a relation between the volume of the inner space which is pumped by a pump electrode per unit area (the volume of the inner space/the area of the pump electrode) and the offset current.

FIG. 6 is a graph showing a relation between the volume of the first inner space 20 which is pumped by the inner pump electrode 22 per unit area (the volume W of the first inner space 20/the area S of the inner pump electrode 22, and hereinafter, referred to also as "ratio W/S") and the offset current. Herein, the area of the inner pump electrode 22 refers to the total area of a surface of the inner pump electrode 22 which is exposed to the first inner space 20. The inner pump electrode 22 has only to be formed on at least one surface of the first inner space 20. Such values of the volume and the area as to obtain the result shown in FIG. 6 are calculated, where the unit of the length is mm. As shown in FIG. 6, when the ratio W/S is in the range from 0.08 to 0.35, the offset current takes an almost constant value of 0.05 µA or less. Particularly, when the ratio W/S is in the range from 0.08 to 0.30, the offset current value is smaller. In contrast to this, when the ratio W/S is less than 0.08 or more than 0.35, the offset current value sharply increases.

The fact that when the ratio W/S is in the range from 0.08 to 0.35, the offset current takes an almost constant value of 0.05 µA or less means that almost no effect of the volume of the inner space is produced on the pumping capability of the pump cell in such a case.

On the other hand, when the ratio W/S is less than 0.08, the offset current value sharply increases. It is thought that this is because the distribution of the oxygen concentration in the first inner space 20 becomes remarkable since only part of the inner pump electrode 22 is effectively used to pump out oxygen ions, and the controllability of the pump cell on the oxygen concentration in the first inner space 20 thereby decreases. Further, when the ratio W/S is more than 0.35, the offset current value sharply increases. It is thought that this is because the controllability of the pump cell on the oxygen concentration in the first inner space 20 decreases since the volume of the gas to be pumped out by the inner pump electrode 22 per unit area increases.

In view of the above fact, the gas sensor 100 of the preferred embodiment is formed so that the ratio W/S may be in the range from 0.08 to 0.35, and more preferably so that the ratio W/S may be in the range from 0.08 to 0.30. In the gas sensor 100 of the preferred embodiment, the offset current value thereby becomes smaller and the variation in the measurement accuracy can be reduced.

(Aspect Ratio of Inner Space)

Next, discussion will be made on the aspect ratio of the inner space.

The above-discussed requirements as to the first inner space 20 also hold as to the second inner space 40. The first inner space 20 and the second inner space 40, however, do not necessarily have to have the same sectional shape. FIG. 7 is a graph showing respective relations between the aspect ratio of the first inner space 20 (the thickness (x1) of the inner space/the width (x2) of the inner space) and the offset current in a case where the first inner space 20 and the second inner space 40 have the same sectional shape and in another case where the first inner space 20 and the second inner space 40 have different sectional shapes. Herein, it is assumed that the first inner space 20 and the second inner space 40 have the same sectional shape when the aspect ratio of the first inner space 20 is the same as that of the second inner space 40 (in other words, when the ratio of these aspect ratios is 1) and the first inner space 20 and the second inner space 40 have different sectional shapes when the aspect ratio of the first inner space 20 is 1.56 times as large as that of the second inner space 40 (in other words, when the ratio of the former to the latter is 1.56).

As shown in FIG. 7, in both the cases, when the aspect ratio of the first inner space 20 is in the range from 0.05 to 0.25, the offset current takes an almost constant value of 0.04 µA or less. Particularly, when the aspect ratio of the first inner space 20 is in the range from 0.05 to 0.23, the offset current is smaller. In contrast to this, when the aspect ratio of the first inner space 20 is less than 0.05 or more than 0.25, the offset current value sharply increases.

Thus, when the aspect ratio of the first inner space 20 is in the range from 0.05 to 0.25, the offset current takes an almost constant value of 0.05 µA or less. This means that if the first inner space 20 has such an aspect ratio as above, regardless of whether the first inner space 20 and the second inner space 40 have the same sectional shape or not, almost no effect of the volume of the inner space is produced on the pumping capability of the pump cell.

On the other hand, when the aspect ratio of the first inner space 20 is less than 0.05, the offset current value sharply increases. It is thought that this is because, as discussed above, only part of the inner pump electrode 22 is effectively used to pump out oxygen ions. Further, when the aspect ratio of the first inner space 20 is more than 0.25, the offset current value sharply increases. It is thought that this is because, as discussed above, the volume of gas to be processed by the inner pump electrode 22 per unit area increases.

In view of the above fact, the gas sensor 100 of the preferred embodiment is formed so that the aspect ratio of the first inner space 20 may be in the range from 0.05 to 0.25, and more preferably so that the aspect ratio of the first inner space 20 may be in the range from 0.05 to 0.23. In the gas sensor 100 of the preferred embodiment, the offset current value thereby becomes smaller and the variation in the measurement accuracy can be reduced. In such a case, whether the first inner space and the second inner space have the same aspect ratio or different aspect ratios, the same effect is produced.

Further, in the gas sensor 100 of the preferred embodiment, it is favorable that the width (x2) of the first inner space 20 is 30 to 85% of the width (x6) of the sensor element 101, and more preferably 40 to 70% of that of the sensor element 101. When the width (x2) of the first inner space 20 is more than 85% of the width (x6) of the sensor element 101, this is not favorable because the internal stress increases and the strength to element breakage decreases. When the width (x2) of the first inner space 20 is less than 30% of the width (x6) of the sensor element 101, this is not favorable because the area of walls in the inner space decrease and the inner pump electrode 22 becomes substantially insufficient.

In view of the above fact, the gas sensor 100 of the preferred embodiment is formed so that the width of the first inner space 20 may be 30 to 85% of the width of the element, and more preferably so that the width of the first inner space 20 may be 40 to 70% of the width of the element. In the gas sensor 100 of the preferred embodiment, the stress of the sensor element 101 is thereby relieved and the occurrence of cracks is inhibited. As a result, the reliability of the gas sensor 100 increases.

Thus, as discussed above, in the preferred embodiment, by determining the position and volume of the inner space in the sensor element 101 within the favorable range, it is possible to achieve the gas sensor 100 in which the variation of measured values is reduced.

While the invention has been shown and described in detail, the foregoing description is in all aspects illustrative and not restrictive. It is therefore understood that numerous modifications and variations can be devised without departing from the scope of the invention.

What is claimed is:

1. A sensor element of a gas sensor for detecting a predetermined gas component in a measurement gas, comprising:
   a solid electrolyte body formed mainly of an oxygen ion conductive solid electrolyte;
   a gas inlet open to an external space for introducing the measurement gas from said external space to inside of said sensor element, said gas inlet formed on a front end surface of said sensor element in a longitudinal direction thereof;
   a first diffusion-controlling part, a second diffusion-controlling part, and a third diffusion-controlling part, each provided as two long horizontal slits;
   an inner space including a first inner space and a second inner space,
   said first inner space communicating with said gas inlet under a predetermined diffusion resistance applied by said first diffusion-controlling part and said second diffusion-controlling part, and said second inner space communicating with said first inner space under a predetermined diffusion resistance applied by said third diffusion-controlling part;
   a main pump cell for pumping oxygen out of said first inner space by applying a predetermined voltage between a first electrode and a second electrode, said first electrode being formed on a surface of said first inner space and said second electrode being formed in a space different from said inner space; and
   an auxiliary pump cell for pumping oxygen out of said second inner space by applying a predetermined voltage between an auxiliary first electrode and said second electrode, said auxiliary first electrode being formed on a surface of said first inner space,
   wherein said gas inlet, said first diffusion-controlling part, said second diffusion-controlling part, said first inner space, said third diffusion-controlling part, and said second inner space are arranged in this order in said longitudinal direction of said sensor element, and
   wherein the length of said first inner space in a short-side direction of said sensor element as viewed from the front end portion side thereof is x1 and the length of said first inner space in said longitudinal direction thereof is x2, $$0.05 \leq x1/x2 \leq 0.25.$$

2. The sensor element according to claim 1, wherein $$0.05 \leq x1/x2 \leq 0.23.$$

3. The sensor element according to claim 1, wherein the distance from a surface of said sensor element in said short-side direction thereof to said inner space is 10% or more of the length of said sensor element in said short-side direction thereof.

4. The sensor element according to claim 1, wherein the length of said inner space in said short-side direction of said sensor element is not less than 7% and not more than 20% of the length of said sensor element in said short-side direction thereof.

5. The sensor element according to claim 4, wherein the length of said inner space in said short-side direction of said sensor element is not less than 10% and not more than 18% of the length of said sensor element in said short-side direction thereof.

6. The sensor element according to claim 1, wherein the volume of said first or second inner space is $W(mm^3)$ and the area of said first electrode is $S(mm^2)$, $$0.08 \leq W/S \leq 0.35.$$

7. The sensor element according to claim 6, wherein $$0.08 \leq W/S \leq 0.30.$$

8. The sensor element according to claim 1, further comprising:
   a buffer space between said first diffusion-controlling part and said second diffusion-controlling part.

9. A gas sensor for detecting a predetermined gas component in a measurement gas, comprising:
   a sensor element which comprises:
      a solid electrolyte body formed mainly of an oxygen ion conductive solid electrolyte;
      a gas inlet open to an external space for introducing the measurement gas from said external space to inside of said sensor element, said gas inlet formed on a front end surface of said sensor element in a longitudinal direction thereof;
      a first diffusion-controlling part, a second diffusion-controlling part, and a third diffusion-controlling part, each provided as two long horizontal slits;
      an inner space including a first inner space and a second inner space,
      said first inner space communicating with said gas inlet under a predetermined diffusion resistance applied by said first diffusion-controlling part and said second diffusion-controlling part, and said second inner space communicating with said first inner space under a predetermined diffusion resistance applied by said third diffusion-controlling part;
      a main pump cell for pumping oxygen out of said first inner space by applying a predetermined voltage between a first electrode and a second electrode, said first electrode being formed on a surface of said first inner space and said second electrode being formed in a space different from said inner space; and
      an auxiliary pump cell for pumping oxygen out of said second inner space by applying a predetermined voltage between an auxiliary first electrode and said second electrode, said auxiliary first electrode being formed on a surface of said first inner space,
      wherein said gas inlet, said first diffusion-controlling part, said second diffusion-controlling part, said first inner space, said third diffusion-controlling part, and said second inner space are arrange in this order in said longitudinal direct of said sensor element, and wherein the length of said first inner space in a short-side direction of said sensor element as viewed from the front end portion side thereof is x1 and the length of said first inner space in said longitudinal direction thereof is x2, $0.05 \leq x1/x2 \leq 0.25$.

10. The gas sensor according to claim 9, wherein $0.05 \leq x1/x2 \leq 0.23$.

11. The gas sensor according to claim 9, wherein the distance from a surface of said sensor element in said short-side direction thereof to said inner space is 10% or more of the length of said sensor element in said short-side direction thereof.

12. The gas sensor according to claim 9, wherein the length of said inner space in said short-side direction of said sensor element is not less than 7% and not more than 20% of the length of said sensor element in said short-side direction thereof.

13. The gas sensor according to claim 12, wherein the length of said inner space in said short-side direction of said sensor element is not less than 10% and not more than 18% of the length of said sensor element in said short-side direction thereof.

14. The gas sensor according to claim 9, wherein the volume of said inner space is W(mm³) and the area of said first electrode is S(mm²), $0.08 \leq W/S \leq 0.35$.

15. The gas sensor according to claim 14, wherein $0.08 \leq W/S \leq 0.30$.

16. The gas sensor according to claim 9, wherein said predetermined gas component is a nitrogen oxide (NOx).

17. The gas sensor according to claim 9, said sensor element further comprising:
a buffer space between said first diffusion-controlling part and said second diffusion-controlling part.

18. A nitrogen oxide (NOx) sensor for detecting a nitrogen oxide (NOx) in a measurement gas, comprising:
a sensor element which comprises:
a solid electrolyte body formed mainly of an oxygen ion conductive solid electrolyte;
a gas inlet open to an external space for introducing the measurement gas from said external space to inside of said sensor element, said gas inlet formed on a front end surface of said sensor element in a longitudinal direction thereof;
a first diffusion-controlling part, a second diffusion-controlling part, and a third diffusion-controlling part, each provided as two long horizontal slits;
an inner space including a first inner space and a second inner space,
said first inner space communicating with said gas inlet under a predetermined diffusion resistance applied by said first diffusion-controlling part and said second diffusion-controlling part, and said second inner space communicating with said first inner space under a predetermined diffusion resistance applied by said third diffusion-controlling part;
a main pump cell for pumping oxygen out of said first inner space by applying a predetermined voltage between a first electrode and a second electrode, said first electrode being formed on a surface of said first inner space and said second electrode being formed in a space different from said inner space; and
an auxiliary pump cell for pumping oxygen out of said second inner space by applying a predetermined voltage between an auxiliary first electrode and said second electrode, said auxiliary first electrode being formed on a surface of said first inner space,
wherein said gas inlet, said first diffusion-controlling part, said second diffusion-controlling part, said first inner space, said third diffusion-controlling part, and said second inner space are arranged in this order in said longitudinal direction of said sensor element, and
wherein the length of said first inner space in a short-side direction of said sensor element as viewed from the front end portion side thereof is x1 and the length of said first inner space in said longitudinal direction thereof is x2, $0.05 \leq x1/x2 \leq 0.25$.

19. The nitrogen oxide (NOx) sensor according to claim 18, said sensor element further comprising:
a buffer space between said first diffusion-controlling part and said second diffusion-controlling part.

* * * * *

UNITED STATES PATENT AND TRADEMARK OFFICE
CERTIFICATE OF CORRECTION

PATENT NO. : 8,398,836 B2
APPLICATION NO. : 12/853527
DATED : March 19, 2013
INVENTOR(S) : Sumiko Horisaka, Sang Jae Lee and Kosuke Nakagawa Page 1 of 1

It is certified that error appears in the above-identified patent and that said Letters Patent is hereby corrected as shown below:

In the Claims

Column 15, line 1

(claim 9, line 37): Please change "arrange" to -- arranged --

Column 15, line 2

(claim 9, line 38): Please change "direct" to -- direction --

Signed and Sealed this
Fourth Day of June, 2013

Teresa Stanek Rea
*Acting Director of the United States Patent and Trademark Office*